US009381136B2

(12) United States Patent

Cronenberg et al.

(10) Patent No.: US 9,381,136 B2
(45) Date of Patent: Jul. 5, 2016

(54) FIXTURING MEMBER AND DEVICE FOR PERMITTING MIXING IN A PEN INJECTOR

(75) Inventors: Richard Cronenberg, Mahwah, NJ (US); Lionel Vedrine, Palo Alto, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 690 days.

(21) Appl. No.: 13/262,033

(22) PCT Filed: Apr. 15, 2010

(86) PCT No.: PCT/US2010/031264
§ 371 (c)(1), (2), (4) Date: Mar. 7, 2012

(87) PCT Pub. No.: WO2010/121045
PCT Pub. Date: Oct. 21, 2010

(65) Prior Publication Data

US 2012/0172793 A1 Jul. 5, 2012

Related U.S. Application Data

(60) Provisional application No. 61/212,702, filed on Apr. 15, 2009.

(51) Int. Cl.
*A61M 37/00* (2006.01)
*A61J 1/20* (2006.01)
*A61J 1/06* (2006.01)

(52) U.S. Cl.
CPC ................ *A61J 1/2096* (2013.01); *A61J 1/062* (2013.01); *A61J 1/201* (2015.05); *A61J 1/2013* (2015.05); *A61J 1/2037* (2015.05); *A61J 1/2072* (2015.05)

(58) Field of Classification Search
CPC .............. A61M 5/204; A61M 5/2448; A61M 2205/581; A61M 2205/582; A61M 5/1782; A61M 5/31596; A61M 2005/2474; A61M 2205/583; A61M 5/24; A61J 1/2096; A61J 1/1406; A61J 2001/2013; A61J 2001/2072; A61J 1/062; A61J 2001/2037; A61J 1/2089; A61J 1/14; A61J 1/2093; A61J 2001/2065; A61J 2200/10
USPC ........................................................... 604/87
See application file for complete search history.

(56) References Cited

U.S. PATENT DOCUMENTS

| | | | |
|---|---|---|---|
| 3,489,147 | A | 1/1970 | Shaw |
| 4,516,967 | A | 5/1985 | Kopfer |

(Continued)

FOREIGN PATENT DOCUMENTS

| | | | |
|---|---|---|---|
| FR | 2302134 | A1 | 9/1976 |
| GB | 1419061 | | 12/1975 |

(Continued)

*Primary Examiner* — Jason Flick
(74) *Attorney, Agent, or Firm* — The Webb Law Firm

(57) ABSTRACT

In one aspect, a fixturing member for fixing a source of flowable material relative to a pen injector so as to permit introduction of the flowable material into the pen injector is provided herein. The fixturing member includes a body having a web with opposing proximal and distal faces. A distal wall extends distally from the distal face of the web, with the distal wall at least partially encompassing a distal chamber. Features are formed on the body for removable mounting onto a pen injector. Also, features are formed on the body for mounting onto a source of flowable material, A cannula extends through the web the cannula having proximal and distal ends with a lumen extending therebetween. The distal end of the cannula is located in the distal chamber and positioned such that, with the member being mounted to a pen injector, the distal end is located to be in the pen injector. The proximal end of the cannula is located proximally of the proximally face of the web such that, with the member being mounted to a source of flowable material, the proximal end of the cannula is located to be in communication with the flowable material. Advantageously, with the subject invention, a fixturing member is provided which facilitates mixing of substances in a pen injector in preparing a pen injector for injection.

24 Claims, 15 Drawing Sheets

(56) References Cited

U.S. PATENT DOCUMENTS

| | | | |
|---|---|---|---|
| 4,874,381 A | 10/1989 | Vetter | |
| 4,968,299 A | 11/1990 | Ahlstrand et al. | |
| 2002/0173748 A1 | 11/2002 | McConnell et al. | |
| 2002/0177819 A1 | 11/2002 | Barker et al. | |
| 2009/0292271 A1* | 11/2009 | Stepovich ............. | A61J 1/2096<br>604/414 |

FOREIGN PATENT DOCUMENTS

| | | | |
|---|---|---|---|
| JP | 8173506 | A | 7/1996 |
| JP | 2002177387 | A | 6/2002 |
| WO | 02076374 | A1 | 10/2002 |
| WO | 2006085546 | A1 | 8/2006 |
| WO | 2009142944 | A1 | 11/2009 |

* cited by examiner

FIXTURING MEMBER AND DEVICE FOR PERMITTING MIXING IN A PEN INJECTOR

FIELD OF THE INVENTION

This invention relates to devices for mixing substances in preparation for injection by a pen injector.

BACKGROUND OF THE INVENTION

Certain drugs or medicaments (those terms being used interchangeably herein) are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. Medicaments may also be provided in other dry or powder form that require reconstitution.

In addition, drugs may be provided as multipart systems which require mix ng prior to administration. For example, one or more liquid (e.g., flowable (slurry or liquid)) components, and/or dry (e.g., powdered or granular) components may be provided in a drug container or delivery device which require mixing prior to administration. The components can be mixed and used to form various administratable drugs, such as insulin.

It is known in the prior art to mix substances using a syringe and a vial. Typically, a flowable material is provided in the syringe which is intended for mixing with a secondary component accommodated in the vial. The septum of the vial is caused t be pierced by the needle of the syringe with the flowable material being urged from the syringe under force of movement of the plunger. With the flowable material in the vial, the vial is agitated so as to cause mixing of the flowable material and the secondary component. Once mixed, the mixed substance is then aspirated into a new syringe. The syringe may then be used for administration of the mixed substance. This arrangement, however, has some drawbacks. Dose size, where less than the entire dose of the mixed substance is required, may be difficult to control accurately. In addition, a syringe is a one-time use device which can not be used for multiple doses over time. Anew syringe is required for each dose administration. Syringes arc difficult to use for self-administration.

Transfer sets, which include a fixturing device, have been developed to facilitate fluid transfer between components in obtaining mixing thereof.

Pen injectors permit good dose-size control, multiple doses over time and are well-suited for self-administration. To achieve mixing of substances in pen injectors, prior art devices have been developed that provide a wet component (e.g., liquid) and a dry component (e.g., powder) in separate chambers of a common container with the container being configured to permit the flow of the wet component to the dry component to cause mixing thereof in preparing an administratable solution for injection. U.S. Pat. No. 4,874,381 to Vetter is directed to an injector having a barrel configured for mixing, while U.S. Pat. No. 4,968,299 to Ahlstrand et al. is directed to a drug cartridge having a barrel configured for mixing. Both Vetter et al. and Ahlstrand et al. disclose typical configurations for mixing where a bypass channel is formed in the barrel of the device. These devices also suffer drawbacks. These containers must be specifically configured for mixing and, typically, are more expensive to manufacture than conventional containers (cartridges, injector barrels). In addition, these containers typically have a substantial amount of wasted dead space (e.g., volume of wasted dead space may be four to five times the volume of the accommodated substance). The excess wasted dead space results in larger-size containers, which may be less convenient to handle and more inaccurate for dosing purposes.

SUMMARY OF THE INVENTION

In one aspect, a fixturing member for fixing a source of flowable material relative to a pen injector so as to permit introduction of the flowable material into the pen injector is provided herein. The fixturing member includes a body having a web with opposing proximal and distal faces. A distal wall extends distally from the distal face of the web, with the distal wall at least partially encompassing a distal chamber. Features are formed on the body for removable mounting onto a pen injector. Also, features are formed on the body for mounting onto a source of flowable material. A cannula extends through the web, the cannula having proximal and distal ends with a lumen extending therebetween. The distal end of the cannula is located in the distal chamber and positioned such that, with the member being mounted to a pen injector, the distal end is located to be in the pen injector. The proximal end of the cannula is located proximally of the proximal face of the web such that, with the member being mounted to a source of flowable material, the proximal end of the cannula is located to be in communication with the flowable material. Advantageously, with the subject invention, a fixturing member is provided which facilitates mixing of substances in a pen injector in preparing a pen injector for injection.

In a further aspect of the subject invention, a mixing device is provided which is useable for introducing flowable material into a pen injector. The mixing device includes a reservoir formed to accommodate a flowable material; a displaceable plunger for urging flowable material from the reservoir; a cannula having proximal and distal ends with a lumen extending therebetween, the proximal end being in communication with the reservoir or selectively communicatable with the reservoir; and, a fixturing member. The fixturing member includes a body having a web with a distal face. A distal wall extends from the distal face of the web, with the distal wall at least partially encompassing a distal chamber. Mounting features are formed on the body for removable mounting onto a pen injection. The distal end of the cannula is located in the distal chamber. Advantageously, the mixing device of the subject invention is capable of introducing flowable material into a pen injector, thus permitting mixing of the flowable material with a secondary material inside the pen injector.

These and other features of the subject invention will be better understood though a study of the following detailed description and accompanying drawings.

DETAILED DESCRIPTION OF THE INVENTION

Figure 1:
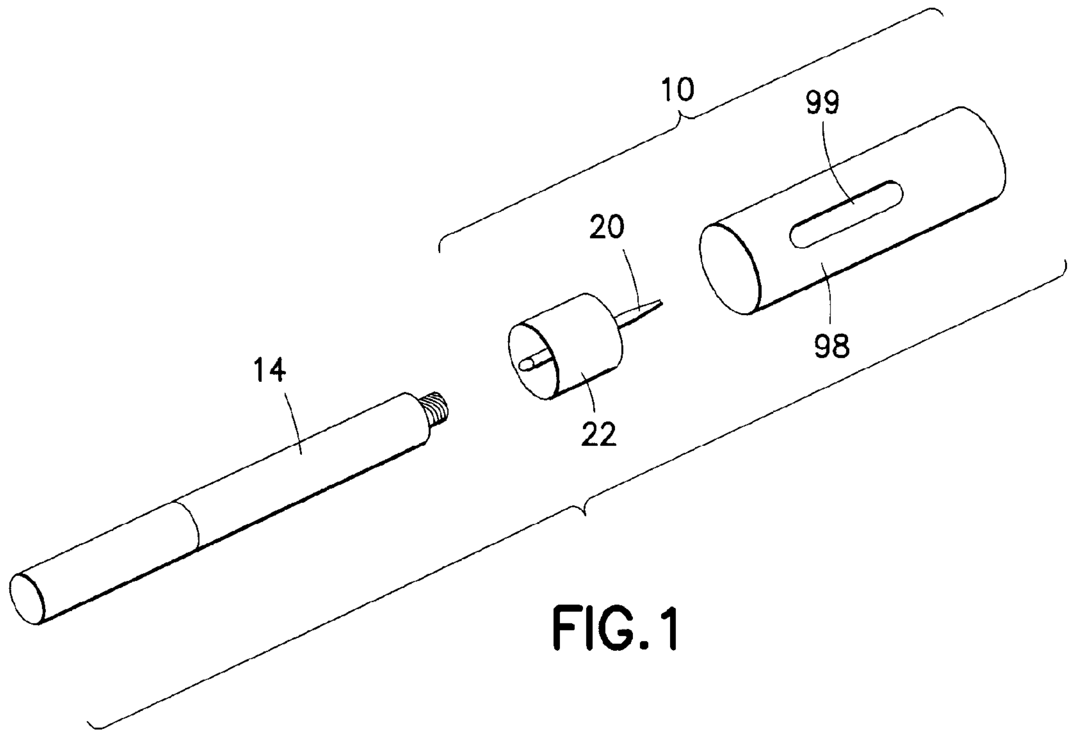
FIG. 1 is an exploded view of an assembly of a pen injector and mixing device.

With reference to the Figures, a mixing device 10 is shown suitable for introducing flowable material 12 into a pen injector 14. The mixing device 10 generally includes a reservoir 16 formed to accommodate the flowable material 12; a displaceable plunger 18 for urging the flowable material 12 from the reservoir 16; a cannula 20; and, a fixturing member 22. The flowable material 12 may be introduced into a reservoir 24 in the pen injector 14 so as to be mixed with a secondary material 26 located therein. In this manner, substances may be mixed inside of the pen injector 14 in forming a mixed solution suitable for injection by the pen injector 14.

As used herein, the term "distal" and derivatives thereof, refer to a direction from the mixing device 10 and towards the pen injector 14, while the term "proximal", and derivatives thereof, refer to a direction away from the pen injector 14 and towards the mixing device 10.

The flowable material 12 may be in any flowable form, such as liquid or slurry. The secondary material 26 may be in any dry (e.g., powder or granular) or wet (e.g., liquid or slurry) state, or a combination thereof. It is to be understood that the term "material" may include one or more constituent elements, with one or more pharmaceutically-active agents. By way of non-limiting examples, the secondary material 26 may be provided in powdered or granular form (e.g., lyophilized powder) with the flowable material 12 being a diluent for reconstituting the secondary material 26. Alternatively, the secondary material 26 may be provided in a wet form, such as liquid or slurry, for combination with the flowable material 12 in preparing a multi-part drug combination.

Figure 4:
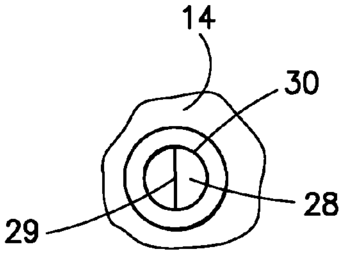
FIG. 4 is a plan view of a slitted septum useable with the subject invention.
Figure 5:
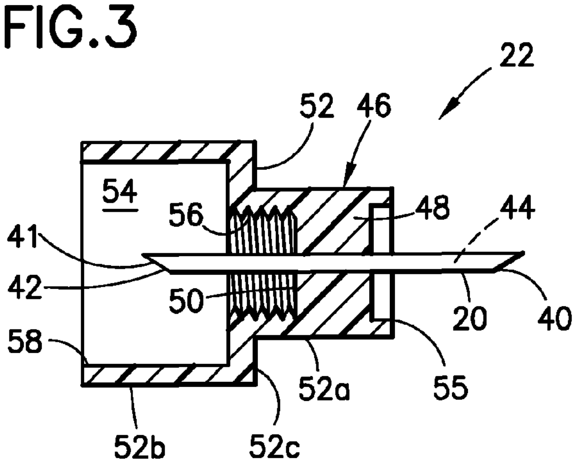
FIG. 5 is a partial cross-sectional view of a fixturing member.
Figure 6:
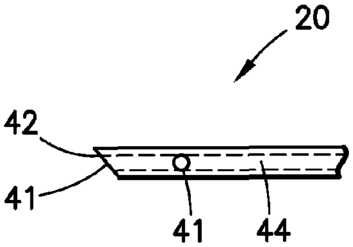
FIG. 6 is a schematic showing possible exit port locations on a cannula useable with the subject invention.

The pen injector 14 may be of any known form. The reservoir 24 is contained within the pen injector 14 and sealed at a proximal end by septum 28 which is accessible through proximal opening 30 of the pen injector 14. The septum 28 is preferably formed of an elastomeric material which is resealable upon being pierced, as is known in the art. The septum 28 may be formed solid (without interruptions or may be slitted with one or more slits 29 (FIG. 4) to permit the cannula 20 to pass therethrough without piercing of the septum 28; the inherent resilience of the slitted septum 28 being such so as to normally close the slit(s) 29 sufficiently tight to define a liquid-tight seal, including after removal of the cannula 20.

The pen injector 14 may be a multi-dosing or single-dosing injector. In addition, the pen injector 14 may include a dose-setting mechanism M, as is known in the art, to set the volume of a dose to be administered. Alternatively, the pen injector 14 may be configured to administer one or more fixed doses.

Needle mounting features 32 are defined on the pen injector 14 about the proximal opening 30. The needle mounting features 32 may be of any known configuration, including threads and/or surface configurations, such as a Luer surface. Preferably, the needle mounting features 32 are defined on a reduced-diameter neck portion 34 extending distally from the proximal opening 30. The needle mounting features 32 and the neck portion 34 are configured to receive a pen needle assembly P for injection, as known in the prior art.

Figure 2:
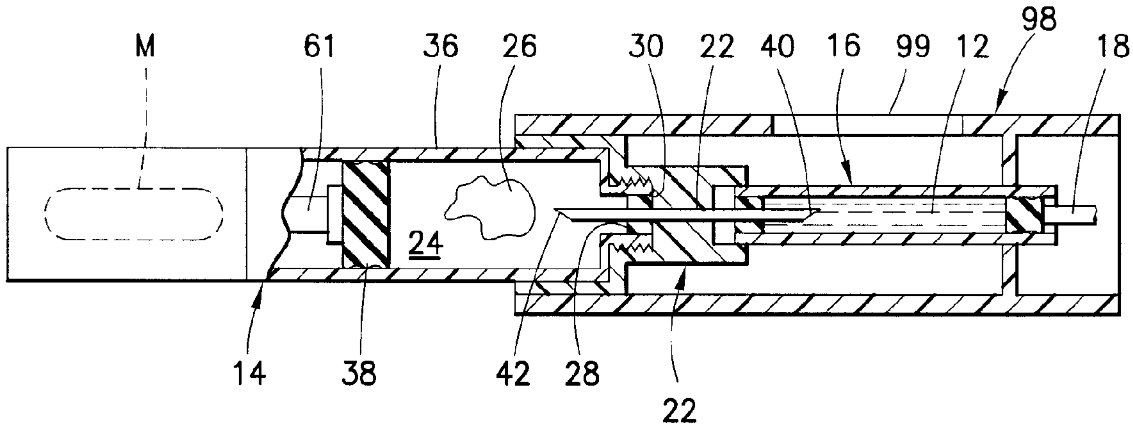
FIG. 2 is a partial cross-sectional view of a mixing device mounted to a pen injector.
Figure 8:
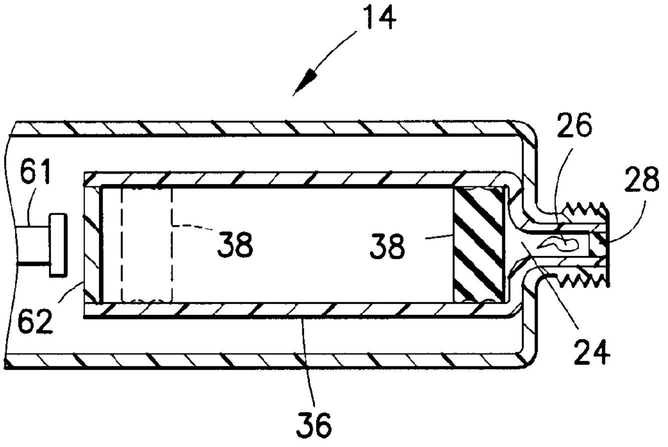
FIGS. 8-16 show different arrangements for limiting pressure build-up in the reservoir of the pen injector during introduction of flowable material, with FIG. 16 being a cross-sectional view taken along line 16-16 of FIG. 15.
Figure 9:
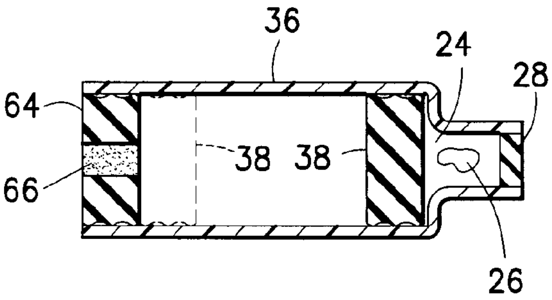

The reservoir 24 is partially defined by a barrel 36 which may be the barrel of a drug cartridge (FIG. 8) contained within the pen injector 14, or the barrel 36 may be a portion of the pen injector 14 (FIG. 2). The barrel 36 may be formed of glass and/or plastic. The septum 28 seals a proximal end of the barrel 36. A stopper 38 may be provided within the barrel 36, so as to be in fluid-tight sliding contact therewith. The reservoir 24 may be defined by the barrel 36, the septum 28, and the stopper 38.

The reservoir 16 of the mixing device 10 may be configured in various manners as discussed below. The plunger 18 may also be formed in various configurations so as to be displaceable in urging the flowable material 12 from the reservoir 16.

The cannula 20 includes a proximal end 40, a distal end 42, and a lumen 44 extending therebetween. The cannula 20 may be a metallic needle cannula, such as those used with medical injections. Alternatively, the cannula 20 may be formed in various materials, such as plastic and/or metal. Preferably, the distal end 42 may he formed to pierce the septum 28, e.g., by being sharpened. Alternatively, the distal end 42 may be formed bluntly, with the septum 28 being slitted. The blunt distal end 42 may be forcibly inserted through the slitted septum 28 without causing piercing thereof.

The cannula 20 includes one or more exit ports 41 at or near the distal end 42 in communication with the lumen 44. The lumen 44 may terminate at one of the exit ports 41 located at the distal end 42. In addition to, or alternatively, one or more of the exit ports 41 may be located spaced from the distal end 42 so as to provide an exit fluid path transverse to the lumen 44. The side port arrangement reduces velocity of the flowable material 12 upon exiting the cannula 20, resulting in reduced turbulence and, thus, possibly reduced foaming during mixing. The distal end 42 may be provided closed with only a side port arrangement being provided.

The fixturing member 22 includes a body 46 having a web 48 with a distal face 50 from which extends a distal wall 52. The distal wall 52 at least partially encompasses a distal chamber 54. Mounting features 56 are formed on the body 46 for removable mounting onto the pen injector 14. Preferably, the mounting features 56 are complementarily formed to cooperate with the needle mounting features 32. More preferably, the mounting features 56 are threads and the needle mounting features 32 are threads formed for threaded engagement therebetween. The pitch and size of the threads of the mounting features 56 need not be the same as the threads of the needle mounting features 56. In this manner, the threads of the mounting features 56 may be formed more coarse than the threads of the needle mounting features 56 so as to permit minimal rotation (e.g., less than one rotation) therebetween for mounting. Various cooperating thread arrangements may be utilized.

The mounting features 56 may include a surface configuration formed to frictionally engage a portion of the pen injector 14. For example, the mounting features 56 may include a surface for frictional engagement with the needle mounting features 32. The mounting features 56 may include a tapered surface for engaging the needle mounting features 32 including a Luer surface. The mounting features 56 may be formed to frictionally engage the needle mounting features 32 even if threaded (e.g., the mounting features 56 may be shaped to frictionally engage the threads of the needle mounting features 32), with or without threaded engagement therebetween. Further, the mounting features 56 may be configured to removably mount onto a portion of the pen injector 14 in addition to, or alternatively, spaced from, the needle mounting features 32. For example, the mounting features 56 may be configured to frictionally engage a portion of the pen injector 14 other than the needle mounting features 32. It is preferred that the mounting features 56 permit removable mounting onto the pen injector 14. Preferably, the mounting features 56 are formed to mount onto the pen injector 14 without special accommodation on the pen injector 14. In this manner, the mounting features 56 may be utilized to mount onto standard pen injectors without modification thereto.

The cannula 20 extends through the web 48, and may be fixed thereto, with the distal end 42 of the cannula 20 being located in the distal chamber 54. With this arrangement, the distal end 42 of the cannula 20 is partially encompassed by the distal wall 52. This arrangement limits access to the distal end 42 in providing shielding to limit contact therewith. In addition, it is preferred that the distal wall 52 be dimensioned to receive a portion of the pen injector 14 in the distal chamber 54 through distal opening 58 defined at the terminus of the distal wall 52. The distal opening 58 provides access to the distal end 42 of the cannula 20. The accommodation of the pen injector 14 within the distal wall 52 restricts sideward movement between the pen injector 14 and the fixturing member 22, when mounted together, thus, limiting strain on the connection.

Figure 7:
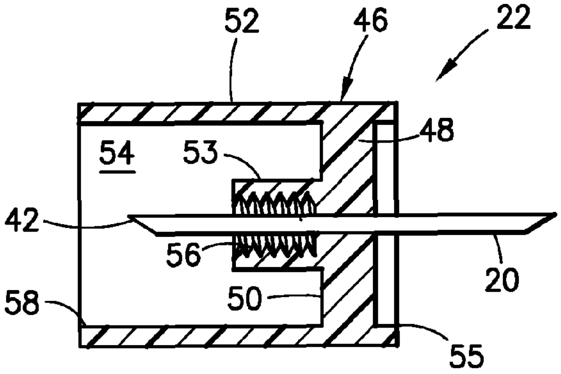
FIG. 7 is a partial cross-sectional view of a fixturing member useable with the subject invention.

The mounting features 56 are preferably formed on the distal wall 52. The distal wall 52 may be formed with a reduced-diameter first portion 52*a*, an enlarged second portion 52*b*, and a shoulder 52*c* defined therebetween. The mounting features 56 may be located on the first portion 52*a* with the first portion 52*a* being configured to allow engagement with the needle mounting features 32 (e.g., the first portion 52*a* may be sized to receive the neck portion 34). The second portion 52*b* may extend from the distal opening 58 and be sized to receive a portion of the pen injector 14 beyond the neck portion 34 (this portion having a larger diameter than the neck portion 34). As an alternative arrangement, as shown in FIG. 7, a secondary wall 53 may be located interiorly of, and separately from, the distal wall 52 with the mounting features 56 being located on the secondary wall 53.

The body 46 is also fixed relative to the reservoir 16. Any known form of fixation may be utilized, including having the body 46 removably fixed relative to the reservoir 16 or rigidly fixed relative to the reservoir 16 (e.g., being formed unitarily with the reservoir 16; being rigidly attached to the reservoir 16). In any regard, the reservoir 16 may be held in a fixed position relatively to the body 46 of the fixturing member 22. One or more engagement members 55 may be formed on the body 46 for removable or fixed mounting onto the reservoir 16, by frictional fit, snap engagement, and/or mechanical interconnection.

Figure 3:
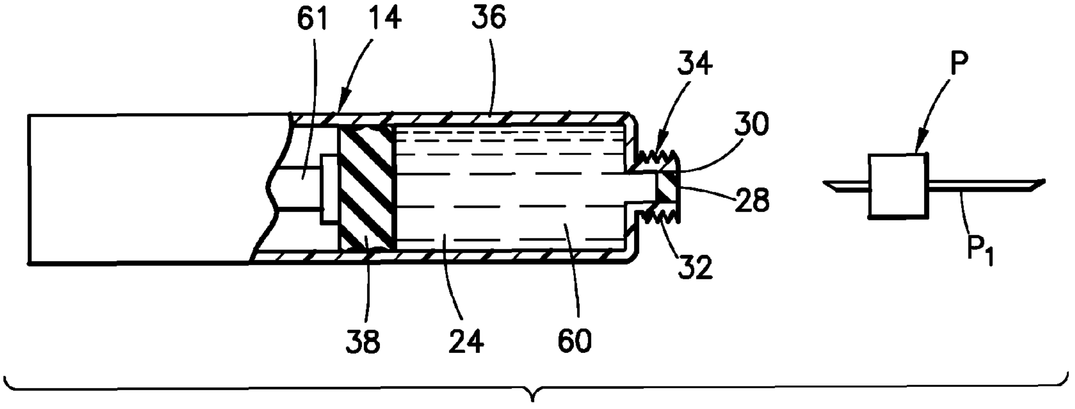
FIG. 3 is an exploded view of a pen injector, having mixed solution therein, with a pen needle assembly.

In use, the mixing device 10 is mounted to the pen injector 14, particularly through mounting of the mounting features 56 onto the pen injector 14. With mounting of the fixturing member 22 onto the pen injector 14, the distal end 42 of the cannula 20 is caused to come into communication with the reservoir 24, particularly with the cannula 20 being caused to pass through the septum 28. With the proximal end 40 of the cannula 20 being in communication with the reservoir 16 of the mixing device 10, the plunger 18 may be caused to be displaced to urge the flowable material 12 from the reservoir 16 and into the reservoir 24 via the cannula 20. Once an effective amount of the flowable material 12 is introduced into the reservoir 24, the fixturing member 22 may be dismounted from the pen injector 14. Preferably, a full stroke of the plunger 18 corresponds to delivering an at least effective amount of the flowable material 12 into the reservoir 24 (a greater than effective amount may be delivered). The flowable material 12 and the secondary material 26 mix inside the reservoir 24 to form a mixed solution 60 (FIG. 3) intended for administration. The pen injector 14 may be agitated to enhance mixing of the flowable material 12 and the secondary material 26. Once sufficiently mixed, a pen needle assembly P may be mounted onto the pen injector 14 to administer a dose of the mixed solution 60. The pen injector 14 includes a plunger 61 which is proximally advanceable through the barrel 36 to cause dose administration of the mixed solution 60, e.g., by driving the stopper 38 proximally. The stroke of the plunger 61 may be set by any known arrangement, including by the dose-setting mechanism M, if provided.

It is noted that air may be trapped in the reservoir 24 before or during the mixing procedure which may cause pressure build-up in the reservoir 24, particularly as the flowable material 12 is introduced therein. This pressure may be relieved with the mounting of the pen needle assembly P onto the pen injector 14, particularly with venting being obtained through the mounted pen needle $P_1$. Preferably, the reservoir 16 is vented as the flowable material 12 is introduced therein so as to minimize, and ideally avoid, the pressure build-up. In one manner, the flowable material 12 may be urged into the reservoir 16 in increments; vertical orientation of the mixing device 10 and the pen injector 14 (with the mixing device 10 being above the pen injector 14) may lead to trapped gases within the reservoir 24 venting through the cannula 20 and into the reservoir 16 in between spurts of the flowable material 12 being introduced into the reservoir 16.

As will be appreciated by those skilled in the art, various configurations may be utilized to prevent pressure build-up in the reservoir 24. In one approach, the stopper 38 may be initially positioned in proximity to the septum 28 so as to minimize the initial volume of the reservoir 24. With minimal volume, minimal air is initially trapped within the reservoir 24, thus lessening the potential for pressure build-up in the reservoir 24 during introduction of the flowable material 12 therein. It is preferred that the stopper 38 be sufficiently spaced from the septum 28 so as to permit the distal end 42 of the cannula 20 to be in communication with the reservoir 24 with the fixturing member 22 being mounted to the pen injector 14. In this manner, embedding of the distal end 42 into the stopper 38 may be avoided. With introduction of the flowable material 12 into the reservoir 24, the stopper 38 is caused to move distally as the volume of the flowable material 12 in the reservoir 24 increases with the stopper 38 eventually stopping with the reservoir 24 at full capacity. A drawback of this approach, however, is, as the size of the reservoir 24 increases, the reservoir 24 is exposed to portions of the barrel 36 located distally of the initial position of the stopper 38. This may result in contamination of the mixed solution 60. Steps to maintain the sterility of the barrel 36, particularly the length of the barrel 36 corresponding to the full size of the reservoir 24, should be taken. A breakable sterility barrier 62 may be applied to the barrel 36, e.g., at a distal end of the barrel 36, located to maintain a sterile zone sufficiently large enough to accommodate the reservoir 24 in its full capacity. The plunger 61 or other component of the pen injector 14 may be utilized to rupture the sterility barrier 62 once the mixed solution 60 has been prepared and injection is desired. Manual interaction may also permit manual removal or rupturing of the sterility barrier 62. As an alternative to the sterility barrier 62, a secondary stopper 64 may be located in the barrel 36 having a vent 66 formed therein. The vent 66 preferably is configured to allow air to pass therethrough while providing a sterile barrier. The secondary stopper 64 is located sufficiently distally of the stopper 38 in the initial state beyond the extent of movement of the stopper 38 in extending the reservoir 24 to full capacity. The vent 66 may be formed by a filter having a pore size of 0.22 microns or smaller to provide the sterile barrier. With the secondary stopper 64, portions of the barrel 36 located distally of the stopper 38 may be maintained sterile, and air displaced by distal movement of the stopper 38 within the barrel 36 may be vented through the vent 66. To later cause injection with this arrangement, both the stopper 38 and the secondary stopper 64 need to be advanced proximally to displace the mixed solution 60 from the reservoir 24 (with the plunger 61 acting against the secondary stopper 64).

Figure 10:
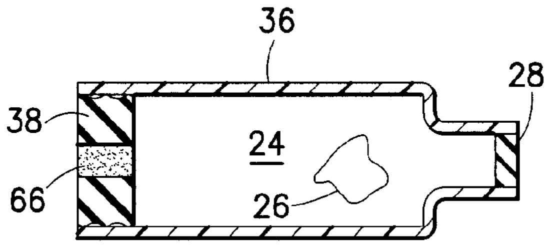

The stopper 38 also may be located in the barrel 36 so as to initially define the full volume of the reservoir 24 with the septum 28. With this arrangement, the stopper 38 need not be moved to cause venting. Here, as shown in FIG. 10, the vent 66 may be provided with the stopper 38 such that any air trapped within the reservoir 24 is vented through the vent 66 with introduction of the flowable material 12 into the reservoir 24. It is noted that, with this arrangement, the vent 66 is in direct communication with the reservoir 24. This may result in inadvertent introduction of moisture into the reservoir 24 prior to use. The moisture may cause premature reconstitution or other adverse effects. To minimize this possibility, the pen injector 14 may be kept in a packaging prior to use having a vapor barrier. It is also noted that, once mixed, some of the liquid of the mixed solution 60 may evaporate through the vent 66, which could affect the dose of the drug being injected. Storing the pen injector 14 in a vapor barrier packing may minimize this potentially detrimental affect.

Figure 11:
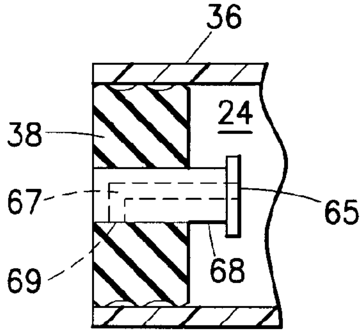
Figure 12:
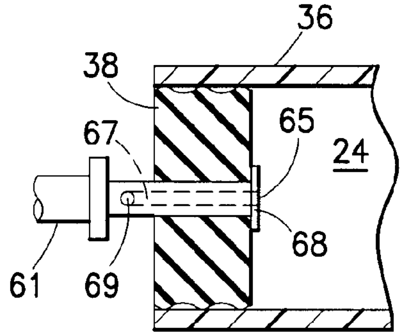

As a further possible configuration, and with reference to FIGS. 11 and 12, the stopper 38 may be located so as to initially define the full volume of the reservoir 24 and be provided with an adjustable valve member 68. The valve member 68 includes a vent passage 67 which, at one end is in communication with the reservoir 24. The vent passage 67 terminates at a vent hole 69 which initially is covered by the stopper 38, so as to be sealed. The valve member 68 is sized to protrude into the reservoir 24 from the stopper 38 in an initial state. With pressure build-up in the reservoir 24, the valve member 68 is caused to shift outwardly with the vent hole 69 becoming uncovered. A stop 65 may be formed on the valve member 68 limiting the extent of outward movement of the valve member 68. Entrapped air may he vented through the vent hole 69. To limit ingress of air into the reservoir 24 after mixing, the valve member 68 may he urged to its closed position (FIG. 11) from its open position (FIG. 12) by the plunger 61. In the closed position, the vent hole 69 is once again covered.

Figure 13:
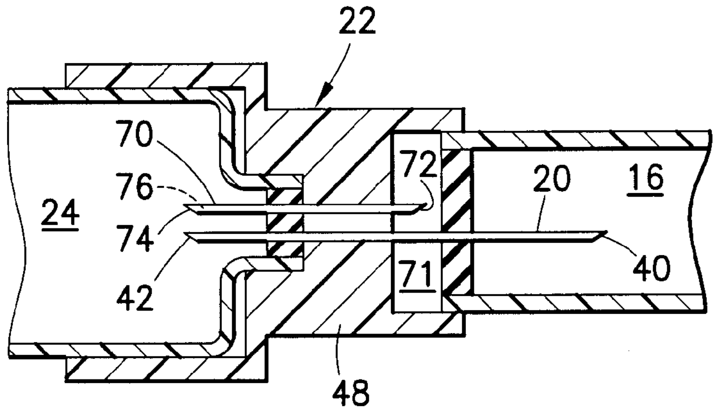

The pressure build-up may be also relieved through the fixturing member 22. As shown in FIG. 13, secondary cannula 70 may be provided extending through the web 48. Preferably, the secondary cannula 70 is fixed to the web 48. The secondary cannula 70 may be formed of various materials, such as metal and/or plastic. The secondary cannula 70 includes a proximal end 72, a distal end 74, with a lumen 76 extending therebetween. The distal end 74 may be formed in the same manner as the distal end 42 of the cannula 20 to pierce the septum 28 or to forcibly pass through the slitted septum 28. The distal end 74 is positioned to be in communication with the reservoir 24 with the fixturing member 22 mounted to the pen injector 14. The proximal end 72 of the secondary cannula 70, however, is located to be vented to ambient and not in communication with the reservoir 16. For example, a space 71 may be defined between the web 48 and the reservoir 16 into which the proximal end 72 is vented. In this manner, as the flowable material 12 is introduced through the cannula 20, pressure built up in the reservoir 24 may be relieved through the secondary cannula 70.

Figure 14:
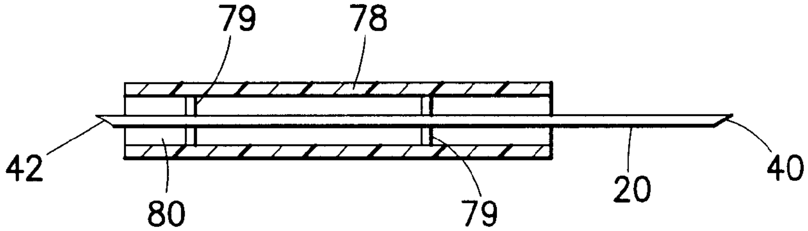
Figure 15:
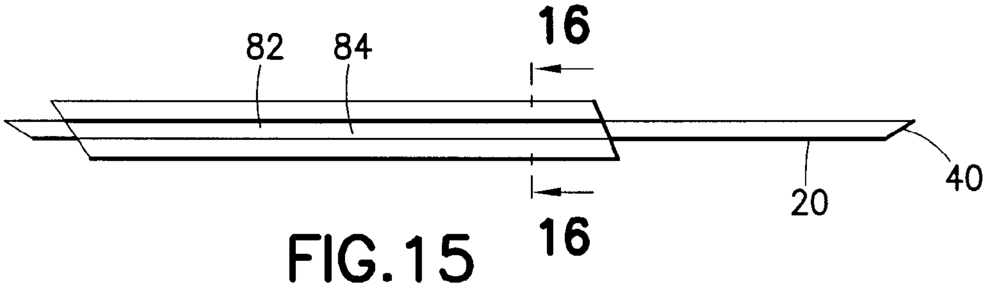
Figure 16:
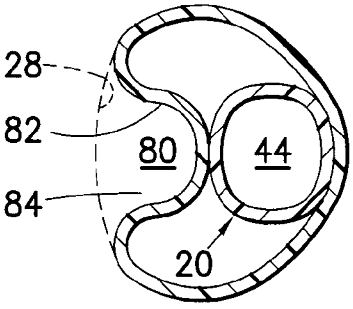

It is further possible to modify the cannula 20 to have a flow path defined therealong, separate from the lumen 44, which would permit venting. For example, as shown in FIG. 14, an outer sleeve 78 may be disposed about the cannula 20 so as to define exteriorly of, and along a portion of the cannula 20, a flow path 80 separate from the lumen 44. The flow path 80 is configured so as to extend from the inside the reservoir 24 to a location permitting ambient venting (e,g., the space 71) with the fixturing member 22 being mounted to the pen injector 14. It is preferred that the flow path 80 not extend into the reservoir 16. The outer sleeve 78 may be supported by struts 79 or be connected in other manners which permit air flow through the flow path 80. The struts 79 may be formed by flattening or otherwise deforming portions of the cannula 20. Alternatively, as shown in FIGS. 15 and 16, an elongated indented tube 82 may be disposed about the cannula 20 so as to define an outer channel 84 along a portion of the cannula 20, the outer channel 84 defining the flow path 80 separate from the lumen 44. Again, it is preferred that the flow path 80 extend from inside the reservoir 24 to a location permitting ambient venting (e.g., the space 71) with the fixturing member 22 being mounted to the pen injector 14. As represented schematically in dashed lines, outer channel 84 is formed with sufficient depth to not be sealed by the septum 28 when passing therethrough. The indented tube 82 may be fixed to the lumen 20 in any known manner.

Figure 17:
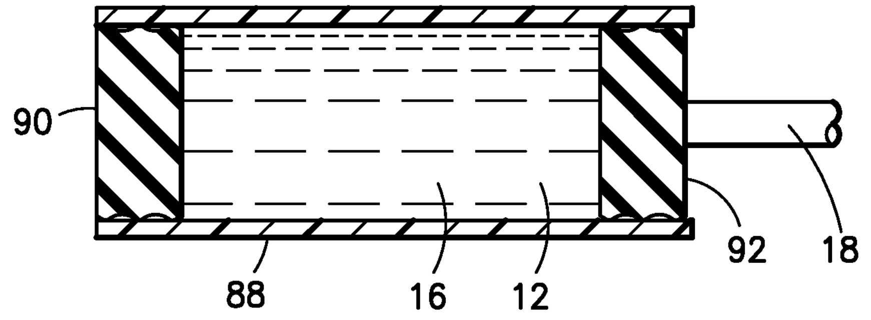
FIGS. 17-19 show different reservoir configurations useable with the mixing device.

The reservoir 24 may be formed with various configurations, as will be appreciated by those skilled in the art. By way of non-limiting example, as shown in FIG. 17, the reservoir 16 may be defined by a barrel 88 having first and second stoppers 90, 92 disposed therein in sliding liquid-tight contact as is known in the art. The barrel 88 may be formed of glass and/or plastic. The first stopper 90 may be positioned to seal a distal end of the barrel 88. The second stopper 92 is spaced proximally from the first stopper 90 so as to define the reservoir between the first and second stoppers 90, 92 within the barrel 88. The plunger 18 is disposed to engage the second stopper 92 in causing movement thereof to urge the flowable material 12 from the reservoir 16. Further, the reservoir 16 may be defined with the barrel 88 having a septum 96 (FIG. 13) sealing a distal end thereof in lieu of the first stopper 90. This configuration is similar to a typical cartridge arrangement.

Figure 18:
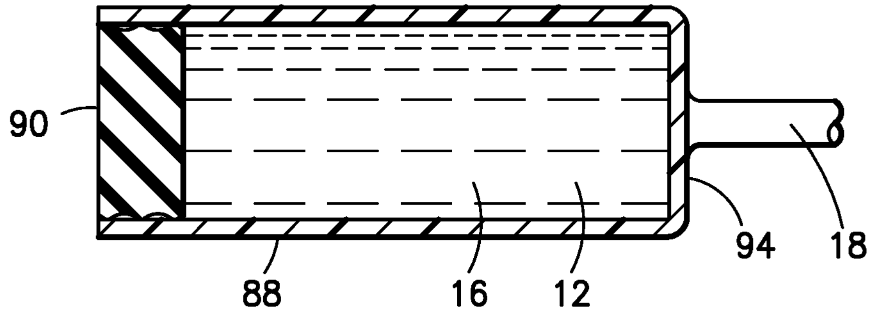

Alternatively, as shown in FIG. 18, the barrel 88 may be formed with a proximal closed end 94, thus eliminating the need for the second stopper 92. To urn the flowable material 12 in this arrangement, the plunger 18 is configured to displace the barrel 88, particularly by urging the closed end 94 towards the first stopper 90. With these various configurations, the cannula 20 is separate from the reservoir 16 and is preferably fixed to the fixturing member 22.

Figure 19:
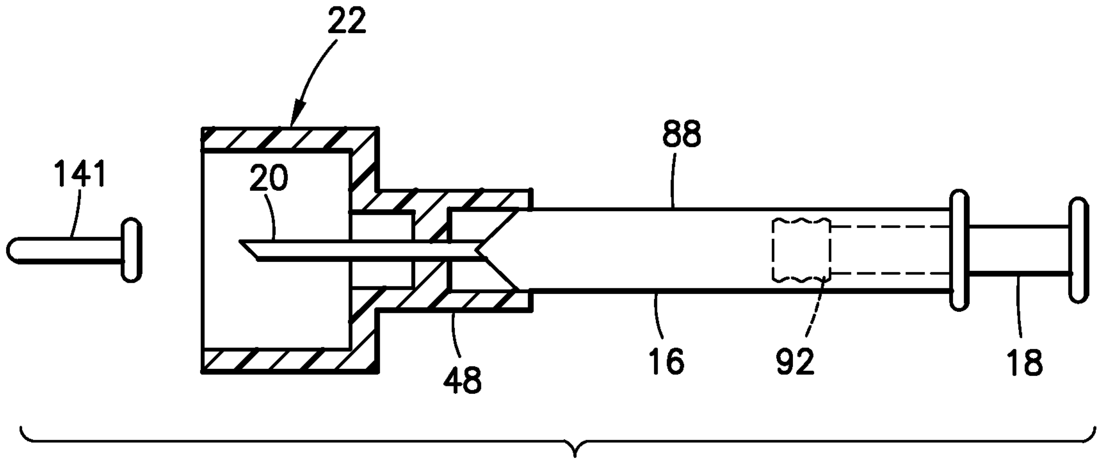
Figure 20:
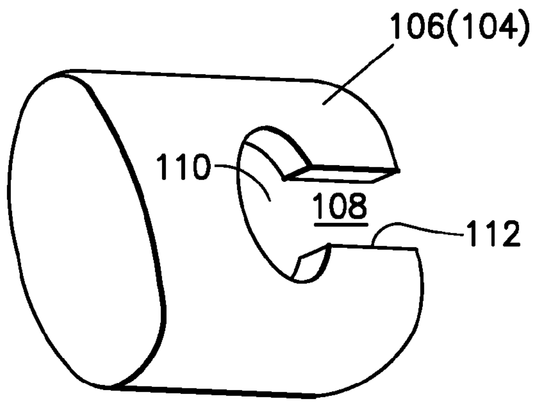
FIGS. 20-29 show different auto-drive arrangements for the plunger of the mixing device.

Alternatively, as shown in FIG. 19, the reservoir 16 may be defined by a syringe-type design where the cannula 20 is fixed to the barrel 88. Only the second stopper 92 is needed for this arrangement. Here, the cannula 20 passes through the web 48, but is not necessarily fixed thereto.

The reservoir 16 may be formed to be removeably mounted to the fixturing member 22, such as through mechanical engagement (e.g., interference fit; snap engagement). The fixturing member 22 may be rigidly fixed to the reservoir 16, such as by interlocking mechanical elements, adhesion and/or fusion. The reservoir 16, the plunger 18 and the fixturing member 22, with the cannula 22, together form the mixing device 10. An outer handling sleeve 98 (FIGS. 1 and 2) may he provided to cover all or a portion of the reservoir 16 to facilitate ease of handling of the mixing device 10. The outer handling sleeve 98 may encompass a substantial portion, or the entirety of, the reservoir 16 to limit tampering therewith. One or more windows 99 may be formed in the outer handling sleeve 98 to permit visual inspection of the reservoir 16 before and after use. The outer handling sleeve 98 may be rigidly or removably fixed to the fixturing member 22, depending on necessity to access the reservoir 16.

The plunger 18 may be driven by any known manner, including being auto- or manually driven. With a manual arrangement, the plunger 18 is accessible from the exterior of the mixing device 86 to receive manually inputted force (FIG. 19). With respect to an auto-drive arrangement, the plunger 18 is held in an initial position against force of a biasing element 100, wherein release from the initial position permits the biasing element 100 to drive the plunger 18 distally and urging the flowable material 12 from the reservoir 16. Various auto-drive arrangements may be utilized with the subject invention. The biasing element 100 is preferably a spring (e.g., coil or compression) formed of any suitable material (e.g., plastic, metal). As will be appreciated by those skilled in the art, the biasing element 100 may be of any design useable to generate a force to drive the plunger 18, including, but not limited to, a deformable resilient member with inherent memory to return to a unbiased state (e.g., an elastomeric member); and, a source of compressed gas releasable to provide the drive force. A spring is shown in the figures as an illustrative example of the biasing element 100.

With respect to FIGS. 20-29, the biasing element 100 is disposed inside of the mixing device 10 and positioned to act against the plunger 18 so as to be capable of urging the plunger 18 in a distal direction. A releaseable retaining arrangement 102 is provided to retain the plunger 18 in an initial position against the force of the biasing element 100. Release of the releaseable retaining arrangement 102 permits the biasing element 100 to drive the plunger 18. Various configurations of the releaseable retaining arrangement 102 may be used as is known in the art. In addition, a trigger 104 may be provided to cause release of the releaseable retaining arrangement 102 upon activation of the trigger 104. The trigger 104 may be utilized where the biasing element 100 does not continually apply an urging force against the plunger 18. For example, where the biasing element 100 includes a source of compressed gas, the compressed gas will be contained prior to use and not act against the plunger 18. Activation by the trigger 104 can result in release of the biasing element 100.

Figure 21:
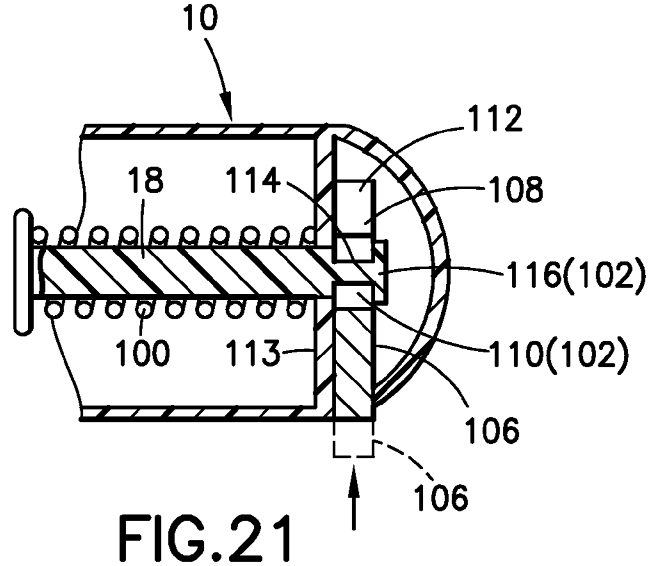

The trigger 104 may be configured to be activated "actively", which requires an act outside of the normal operation of the mixing device 10. In addition, the trigger 104 may be configured to be "passively" activated, where activation is caused as a result of normal operation of the mixing device 10. By way of non-limiting example, and with reference to FIGS. 20 and 21, the trigger 104 in an active configuration may be an axially-shiftable block 106 having an activation slot 108 formed therein. The block 106 is located proximally of a protruding wall 113, which restricts distal movement of the block 106. The activation slot 108 includes an opening 110 from which extends a reduced diameter neck 112. The plunger 18 is formed with a slot 114, configured to he interferingly engaged by the block 106 about the neck 112, and with a stop section 116 proximal to the slot 114. The stop section 116 has a larger diameter than the neck 112. In an initial state, the interengagement of the stop section 116 against the block 106 inhibits distal movement of the plunger 18 under force of the biasing element 100. For activation, the block 106 may be axially shifted to align the opening 110 about the slot 114, as shown in FIG. 21. The opening 110 is sized to permit passage therethrough of the stop section 116. Once shifted, the opening 110 comes into alignment with the stop section 116, thus releasing the plunger 18 and permitting distal movement under force of the biasing element 100. The block 106 may be maintained in the initial, pre-activation state by frictional engagement between the neck 112 and the slot 114; compressive force generated between the stop section 116 and the protruding wall 113; and/or, a secondary component, such as a spring, one or more mechanical features (e.g., detent, ramp), adhesive, and/or fused joint, configured to maintain the block 106 in the initial, pre-shifted state.

Figure 22:
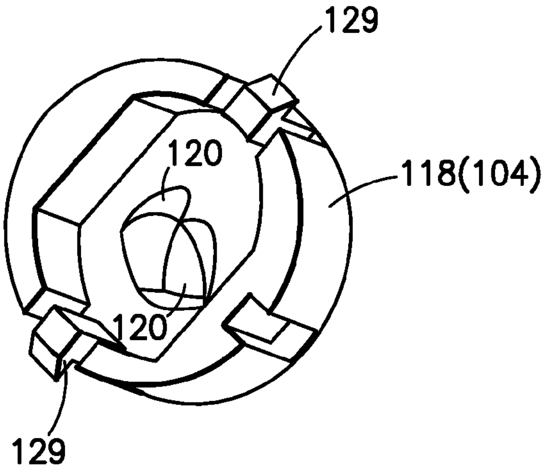
Figure 24:
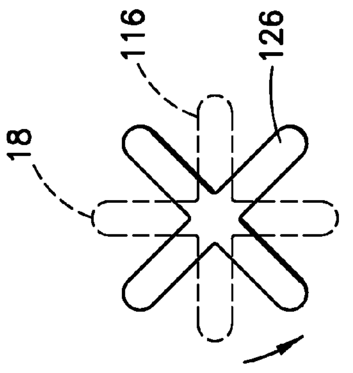
Figure 23:
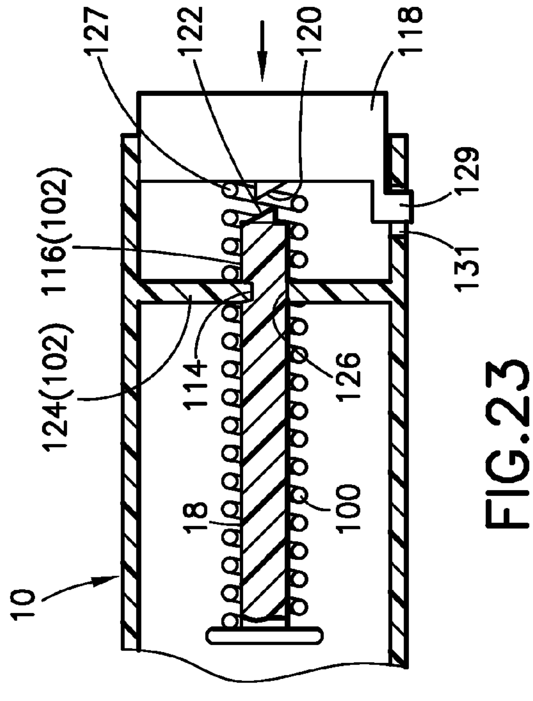
Figure 25:
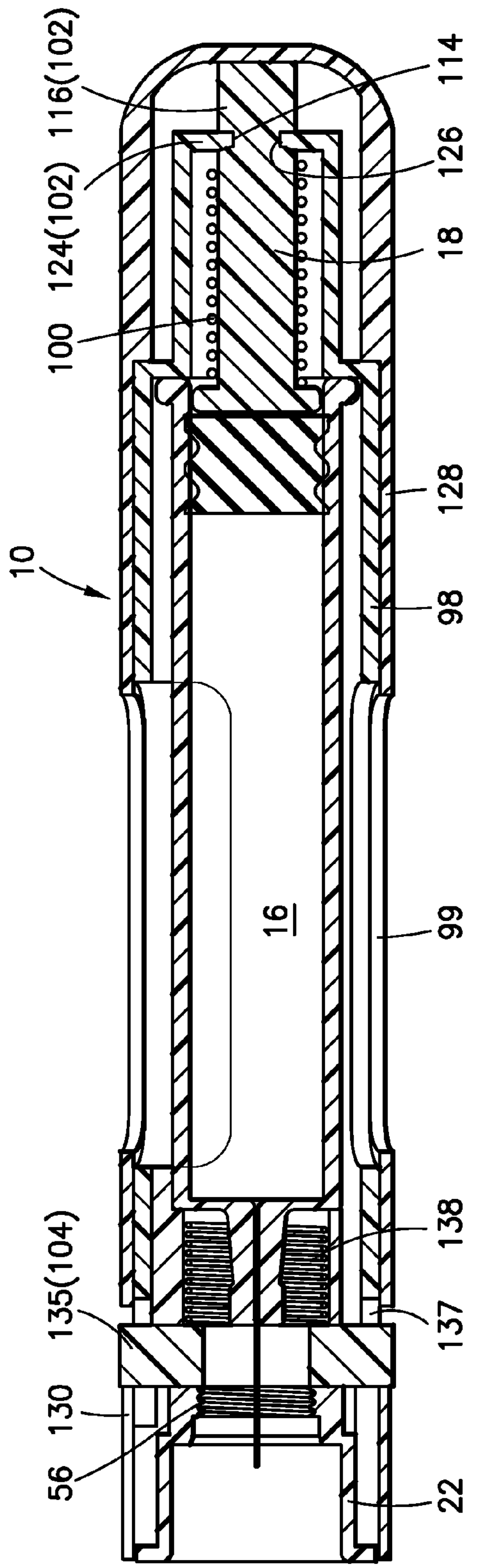
Figure 26:
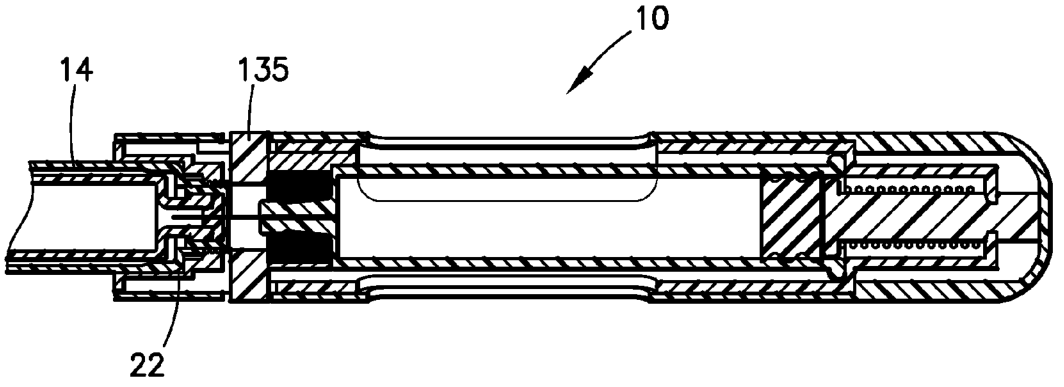

With reference to FIGS. 22-24, the trigger 104 may be in the form of an axially shiftable button 118 which is coaxially aligned with the plunger 18. One or more ramped surfaces 120 may be formed on the button 118 to face the plunger 18 with complementary ramped surfaces 122 being provided on the plunger 18. The complementary ramped surfaces 122 are configured so as to cause rotation of the plunger 18 with sufficient axial movement of the button 118 upon being depressed. The plunger 18 may be provided with the slot 114 seated on a protruding wall 124 with the stop section 116 interengaging therewith to inhibit movement of the plunger 18. The protruding wall 124 is configured such that with sufficient turning of the plunger 18, the stop section 116 is moved clear of the protruding wall 124 so as to permit movement of the plunger 18. An opening 126 may be formed in the protruding wall 124 with the slot 114 being seated therein. Preferably, the opening 126 is non-circular. In addition, the stop section 116 is preferably formed with a profile sized and shaped similar to the opening 126. Accordingly, with the stop section 116 being properly aligned with the opening 126, the stop section 116 may pass through the opening 126. In addition, with the stop section 116 being radially misaligned with the opening 126, the stop section 116 may not pass through the opening 126. As shown in FIG. 24, the plunger 18 is maintained in the initial state, with the stop section 116 being out of alignment with the opening 126. With rotation of the plunger 18, the stop section 116 may be brought into radial alignment with the opening 126. This arrangement may be achieved by forming the stop section 116 and the opening 126 with x-shaped profiles. The button 118 may be maintained in an initial, pre-activation state by a secondary spring 127 disposed between the button 118 and the protruding wall 124. The button 118 may be also retained in the initial state by a releasable retaining arrangement including mechanical, adherent, and/or fused interactions. One or more wings 129 may extend radially from the button 118 to ride along guide slots 131 formed in surrounding portions of the mixing device 10. Interengagement of the wings 129 and the ends of the guide slots 131 limits proximal movement of the button 118 away from the plunger 18.

The trigger 104 may be caused to be passively activated such as during the mounting of the fixturing member 22 onto the pen injector 14. In this manner, no additional action is required to activate the trigger 104 beyond normal usage. By way of non-limiting example, and with reference to FIGS. 25-29, the plunger 18 is configured to be seated in the opening

Figure 27:
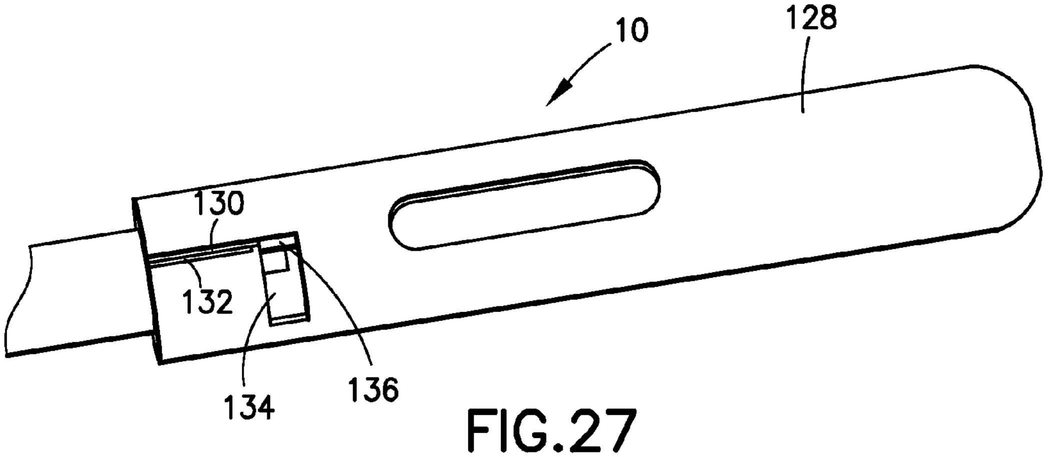
Figure 28:
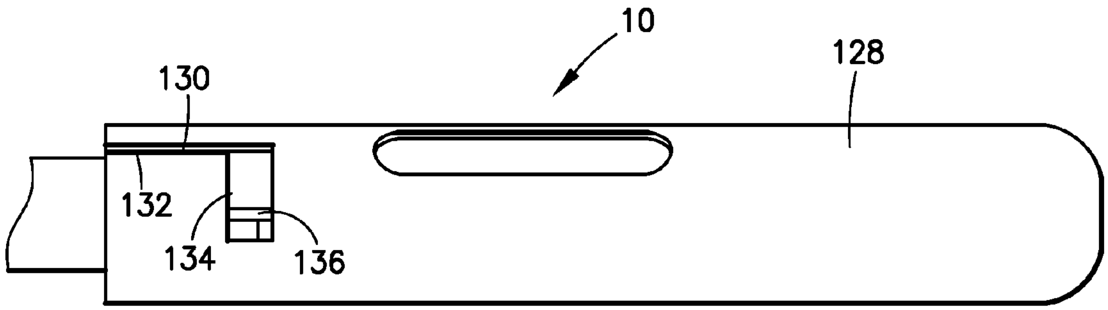

126 as described above with respect to FIGS. 22-24. A rotatable activation sleeve 128 is fixed to the plunger 18 so as to be rotatable therewith. The activation sleeve 128 includes an activation slot 130 having a first axial portion 132 and a second portion 134 disposed transversely to the first axial portion 132. The trigger 104 is in the form of a ring 135 having a tab 136 extending radially outwardly therefrom positioned to be seated in the first portion 132 of the activation slot 130 in an initial state. A secondary spring 138 is disposed to act against the ring 135 in urging the ring 135 to the initial state. The ring 135 is located in a clearance slot 137 defined in the body 46 of the fixturing member 22. The clearance slot 137 defines the limits of axial movement of the ring 135. In the initial state, the ring 135 is located at the distal extreme of the clearance slot 137. The mounting features 56 of the fixturing member 22 are located such that mounting of the fixturing member 22 to the pen injector 14 causes proximal displacement of the tab 136 traversing proximally the first portion 132 of the activation slot 130. With the full mounting of the pen injector 14 to the fixturing member 22, the tab 136 is in alignment with the second portion 134 of the activation slot 130, as shown in FIG. 27. The biasing element 100 is provided with a torsional component which seeks to rotate the plunger 18. Rotation of the plunger 18 is inhibited by the interengagement of the tab 136 with the first portion 132 of the activation slot 130. With the tab 136 coming into the second portion 134 of the activation slot 130, the biasing element 100 causes rotation of the plunger 18 with the tab 136 moving along the second portion 134, as shown in FIG. 28. As a result, the plunger 18 is caused to rotate with the stop section 116 coming into radial alignment with the opening 126.

Figure 29:
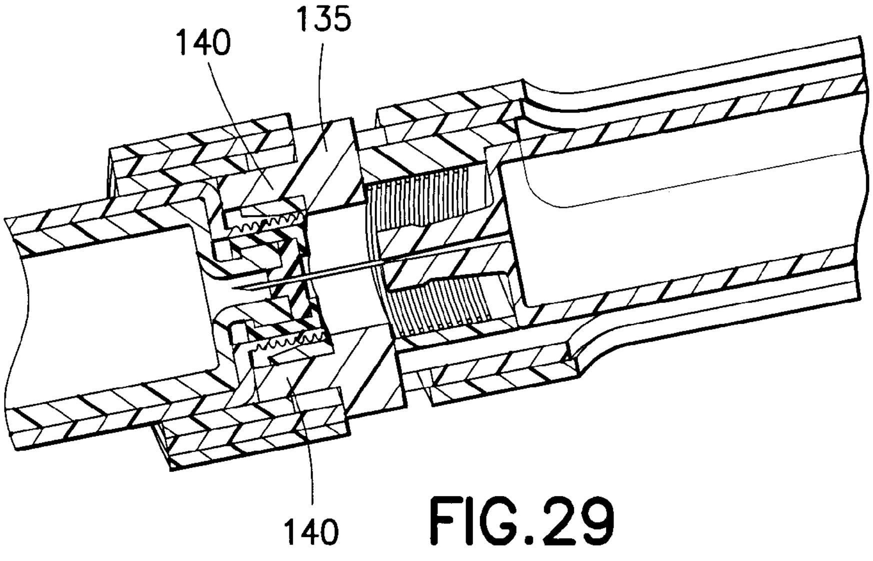

The ring 135 may be configured to be acted against various portions of the pen injector 14 including by the neck portion 34, or other portions of the pen injector 14. With reference to FIG. 29, one or more legs 140 may extend from the ring 135 to engage various portions of the pen injector 14.

Figure 30:
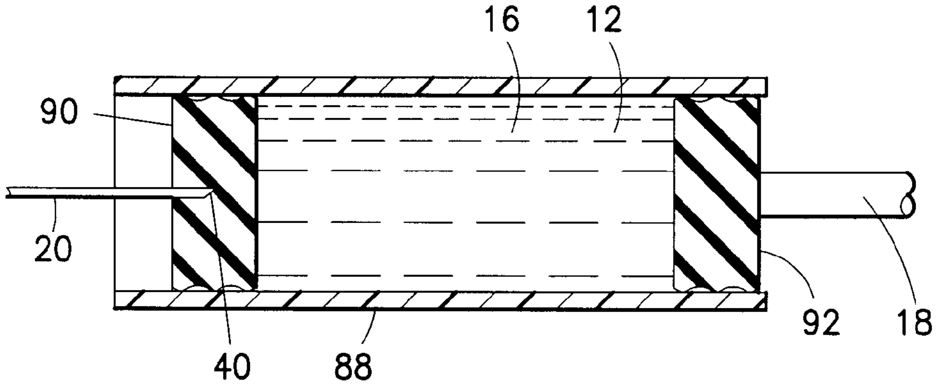
FIGS. 30-36 show different arrangements for permitting selective communication between the cannula and the reservoir of the mixing device.
Figure 31:
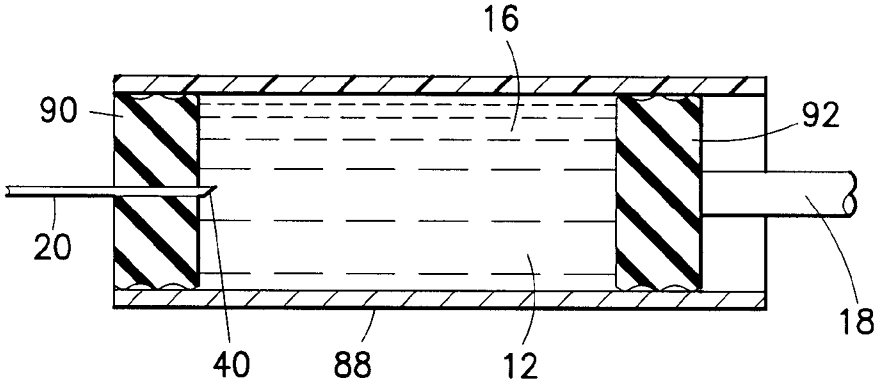
Figure 32:
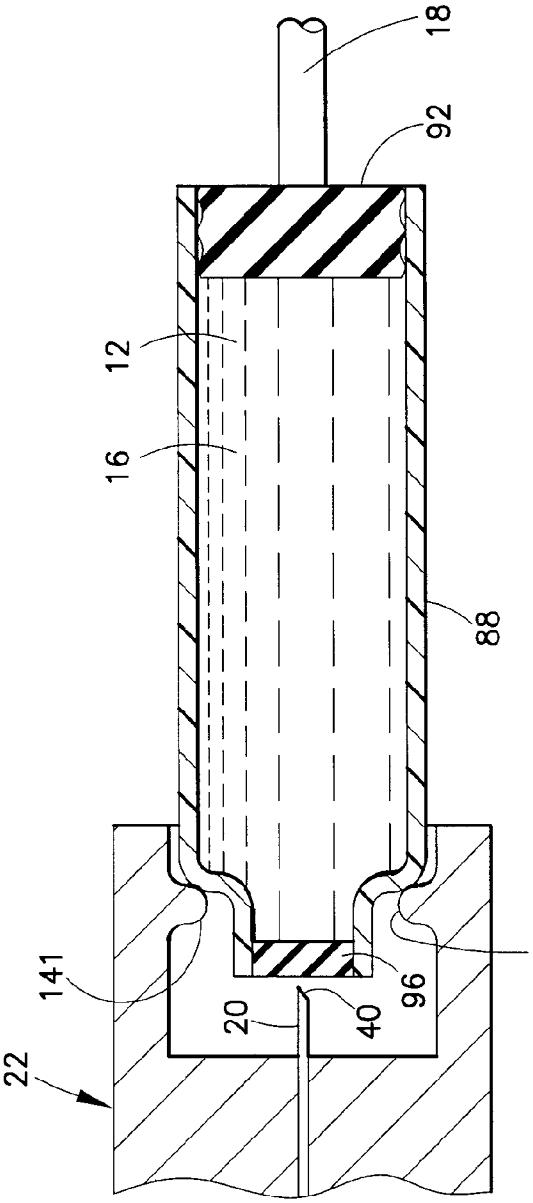
Figure 33:
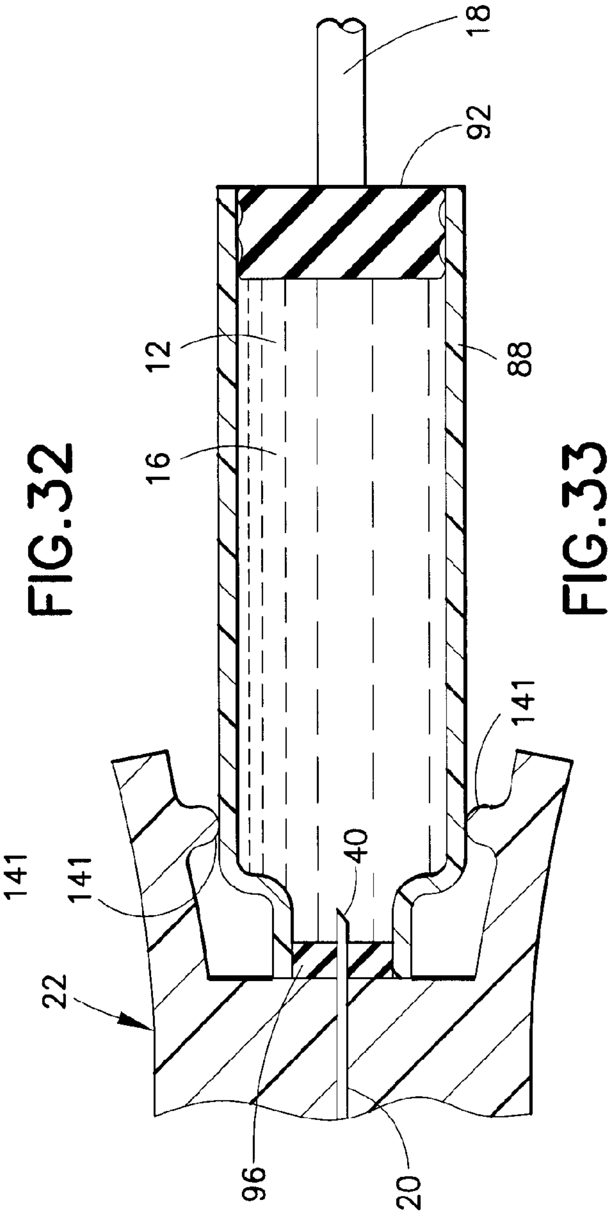

It is preferred that the reservoir 16 be sealed prior to use. More specifically, it is preferred that the cannula 20 not be in communication with the reservoir 16 prior to use. With the cannula 20 fixed to the reservoir 16, this is not achievable. With this arrangement, a plug 141 or other seal member (FIG. 19) may be provided for the distal end 42 of the cannula 20 prior to use. Sealing of the distal end 42 results in sealing of the reservoir 16. With respect to the other configurations of the reservoir 16, particularly where the cannula 20 is not fixed to the reservoir 16, the first stopper 90 or the septum 96 may be located at least partially proximally of the proximal end 40 of the cannula 20, as shown in FIG. 30. The proximal end 40 may be spaced from or partially embedded into the first stopper 90/septum 96 so as to not be initially in communication with the reservoir 16. The proximal end 40 of the cannula 20 may be forced completely through the first stopper 90 or the septum 96 to come into communication with the reservoir 16, as shown in FIG. 31. In one arrangement, force of movement of the plunger 18 may cause displacement of the first stopper 90 by force being transmitted through the flowable material 12 (the flowable material 12 being considered to be relatively incompressible). It is preferred that the barrel 88 be held stationary in this arrangement. With reference to FIGS. 32-33, with the septum 96 being secured to the barrel 88, force of movement of the plunger 18 may result in displacement of the entire reservoir 16 with the cannula 20 being forced completely through the septum 96. The reservoir 16 may be held in an initial state by retaining members 141 formed to engage the reservoir and inhibit movement thereof (e.g., the retaining members 141 may be one or more detents seated below the barrel 88 to resist distal movement thereof). The retaining members 141 are preferably formed on the fixturing member 22, but may be located at other locations on the mixing device 10. With the plunger 18 being driven forward, force is applied to the reservoir 16 which eventually causes the reservoir 16 to surmount the retaining members 141 thereby causing distal movement under force of the plunger 18. The distal movement may be limited by engagement with the fixturing member 22.

Figure 34:
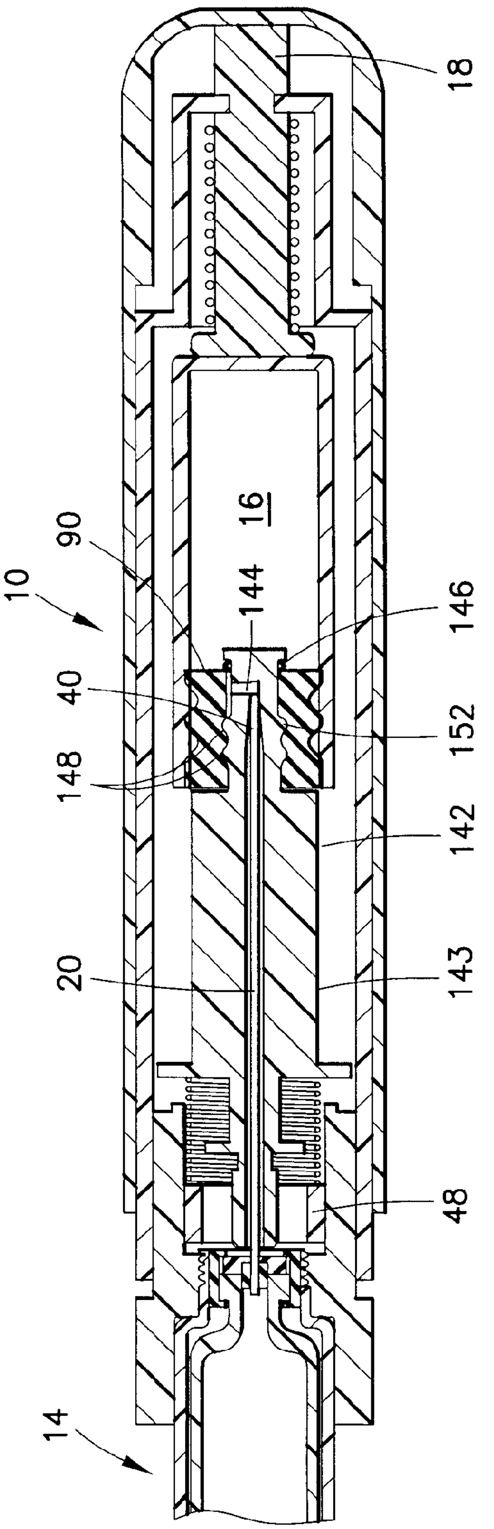
Figure 35:
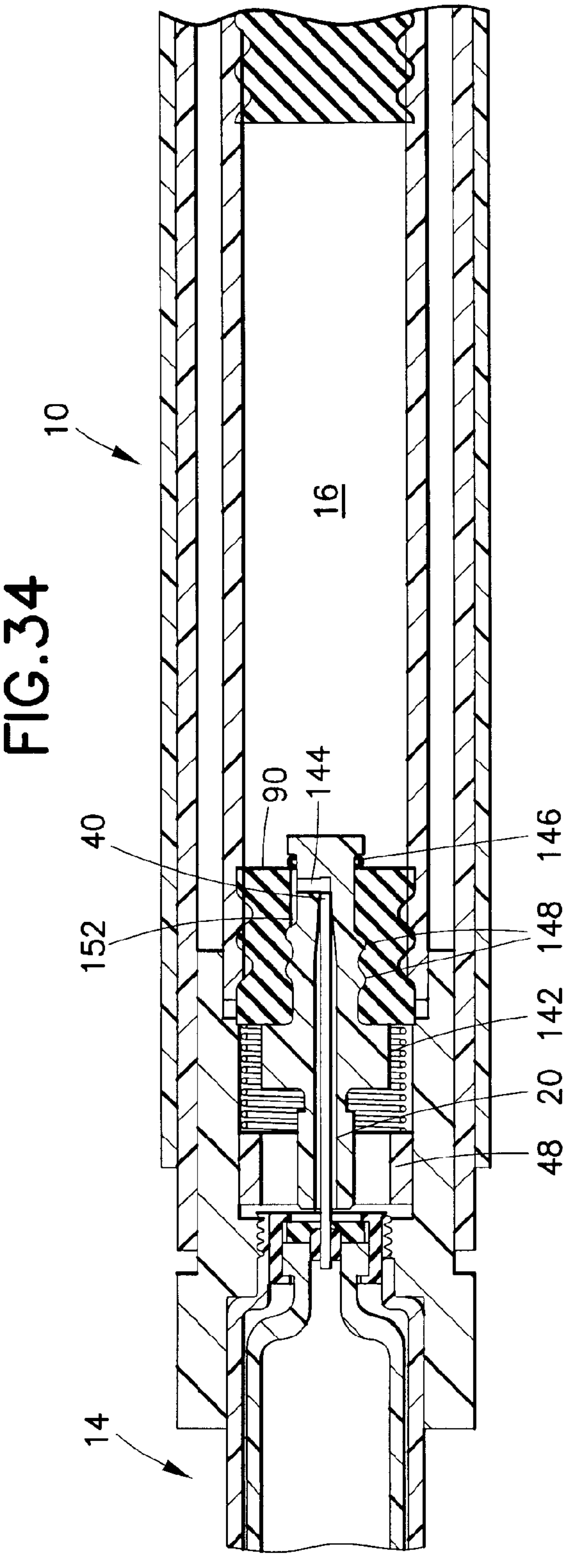
Figure 36:
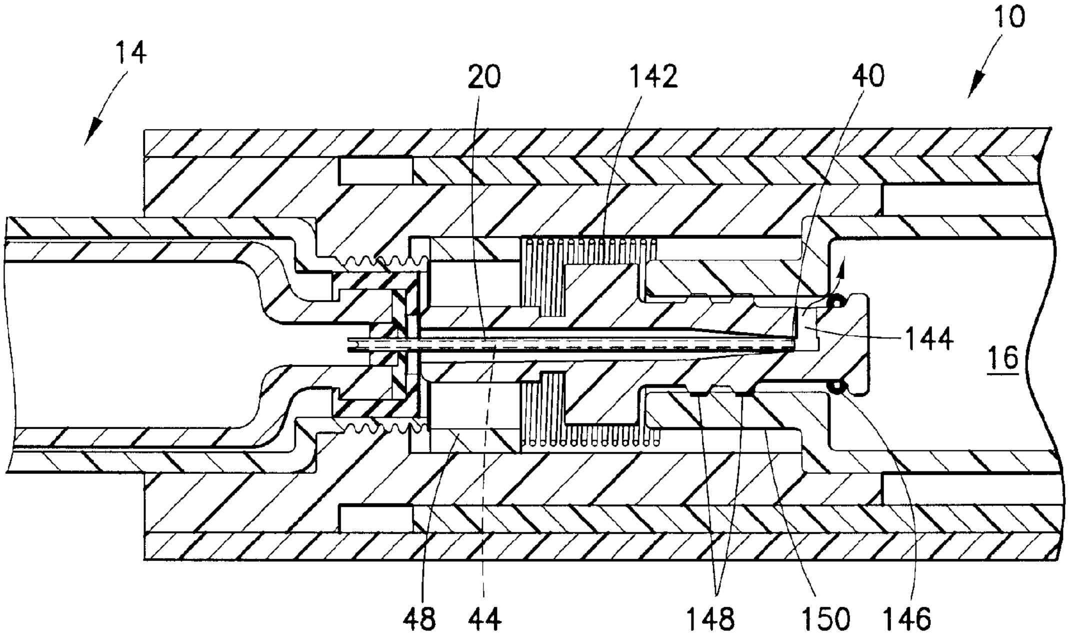

Other arrangements for permitting selective communication between the cannula 20 and the reservoir 16 may be utilized, such as through the use of a valve 142. The cannula 20 may be embedded in the valve 142 with an exit passage 144 defined in the valve 142 in communication with the lumen 44, particularly through the proximal end 40. One or more seals 146 are formed on the valve 142 to define a liquid tight seal between the exit passage 144 and the reservoir 16 in an initial state (FIG. 34). The valve 142 is displaceable so that the exit passage 144 may come into communication with the reservoir 16 (FIG. 35), thereby permitting communication with the lumen 44 of the cannula 20. Secondary seals 148 may be provided to define a liquid tight seal distally of the exit passage 144. The valve 142 may be formed to extend through the web 48 such that mounting of the pen injector 14 onto the fixturing member 22 results in displacement of the valve 142 from a closed position, where the exit passage 144 is sealed, to an open position, where the exit passage 144 is in communication with the reservoir 16. The valve 142 may engage a reduced diameter throat portion 150 (FIG. 36) formed to extend from the barrel 88. Alternatively, the valve 142 may pass through passage 152 (FIGS. 34 and 35) formed in the first stopper 90 or the septum 96. The valve 142 also may be provided with a stop block 143 (FIG. 34) positioned to engage the first stopper 90. The stop block 143 may be used to restrict movement of the stopper 92. With the reservoir 16 being configured as described and shown in FIG. 18, the barrel 88 may be advanced distally relative to the stopper 92 to urge the flowable material 12 from the reservoir 16.

The mixing device 10 may be provided with one or more indicators to provide a visual, audible and/or tactile indication that the pen injector 14 is properly mounted to the fixturing member 22 and/or to provide end-of-stroke indication for the plunger 18. With reference to the use of the ring 135 discussed above, the position of the tab 136 in the activation slot 130 will provide visual indication of proper mounting of the pen injector 14. In particular, with the tab 136 coming into alignment with the second portion 134 of the activation slot 130, indication is provided that full mounting has been achieved. One or more interengaging members also may be formed on the activation sleeve 128 and/or the ring 135 so as to provide a clicking noise and/or a tactile response with the activation sleeve 128 sufficiently rotating relative to the ring 135.

Figure 37:
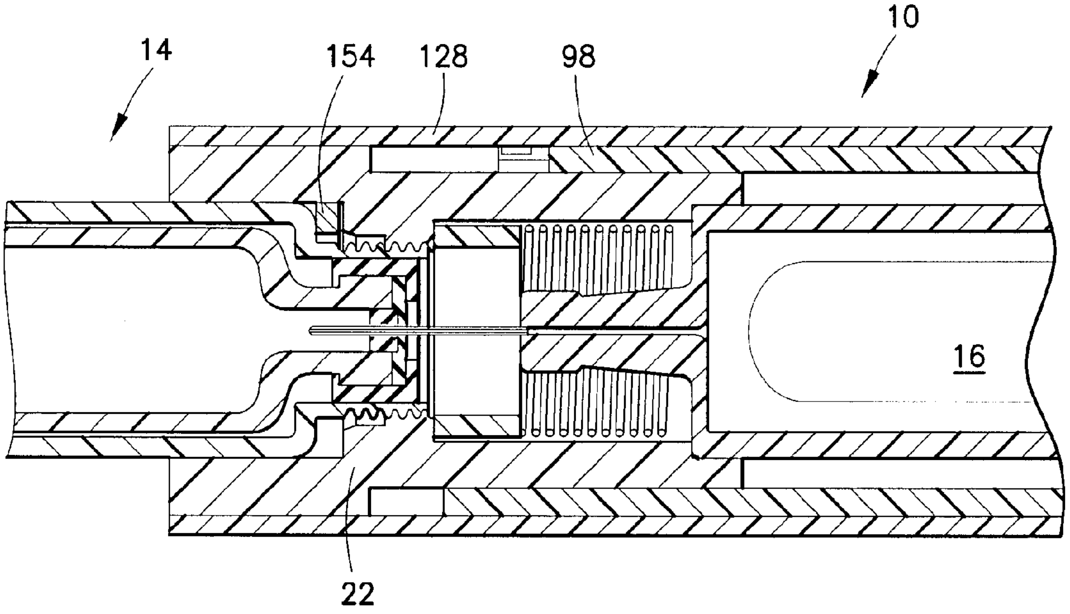
FIGS. 37-39 show an arrangement for providing indication of proper mounting of a pen injector to the mixing device; and, FIGS. 40-43 show an arrangement for providing end-of-stroke indication for the plunger completing its stroke within the mixing device.
Figure 38:
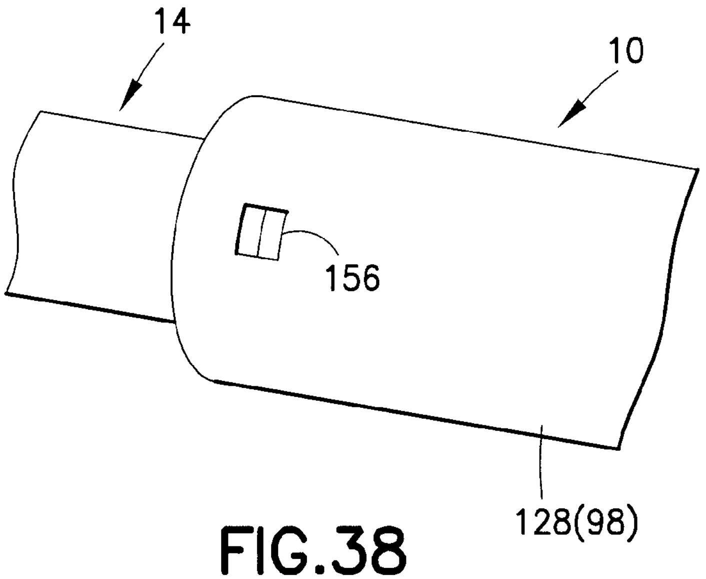
Figure 39:
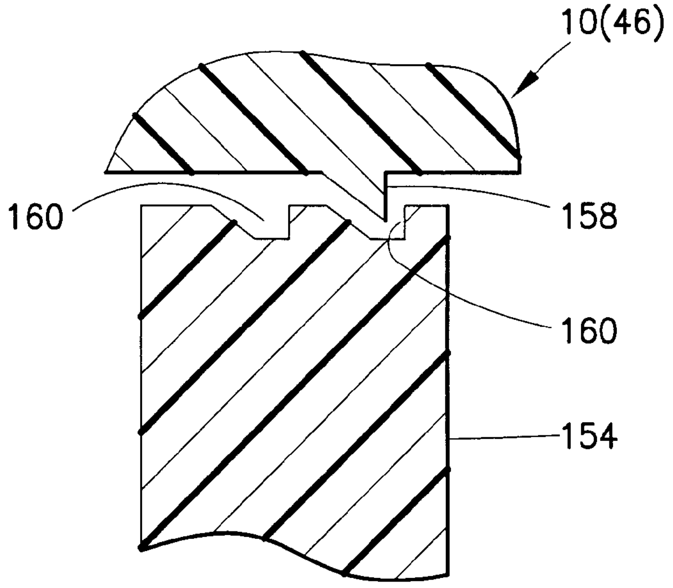
Figure 40:
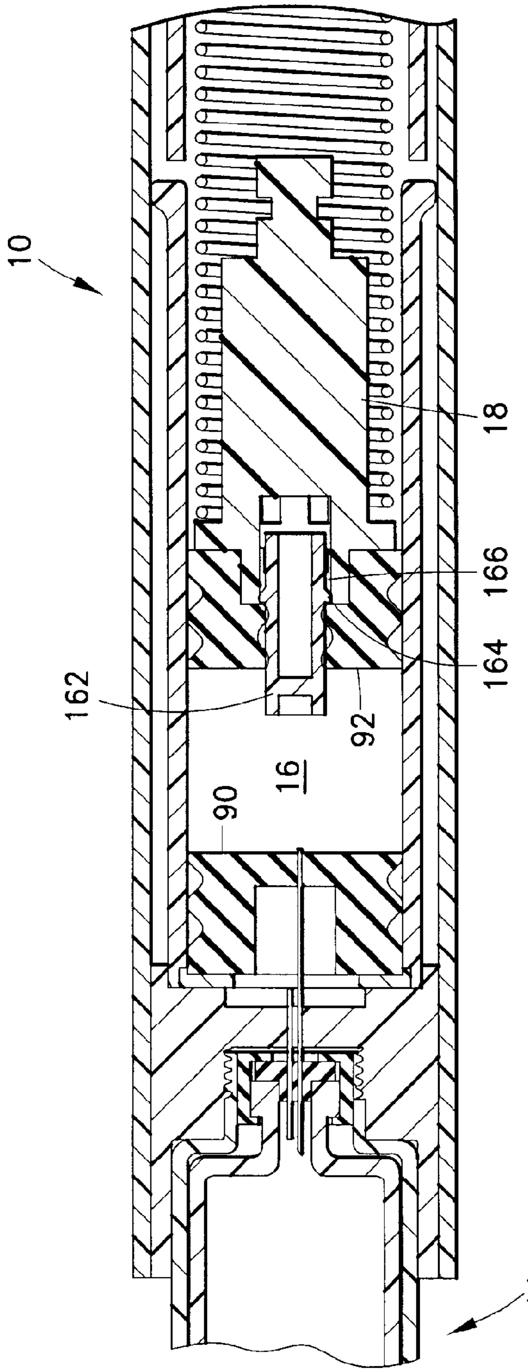
Figure 41:
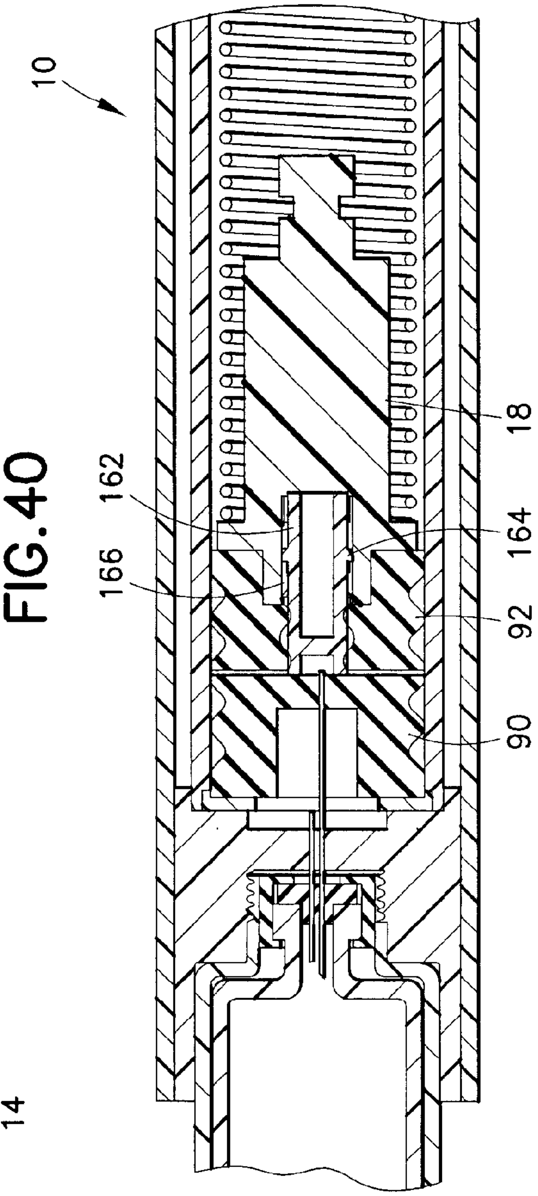
Figure 43:
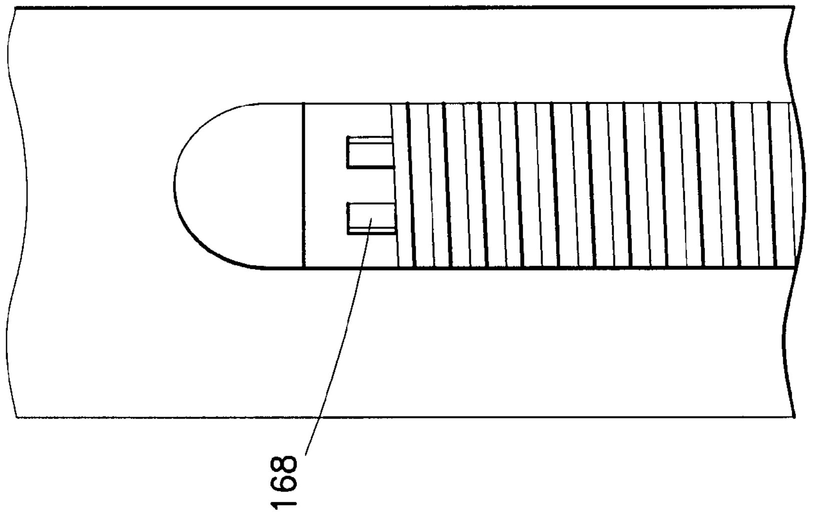
Figure 42:
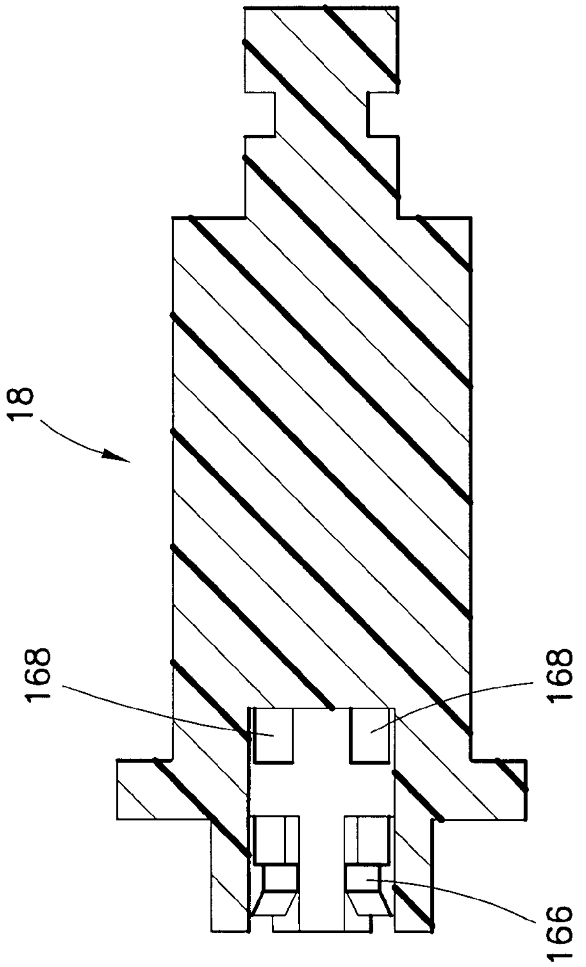

In addition, as shown in FIGS. 37-39, an indicator ring 154 may be located within the fixturing member 22 so as to be displaceable by the pen injector 14 during mounting of the pen injector 14 to the fixturing member 22. Preferably, the indicator ring 154 is formed of a different color from the outermost portion of the mixing device 10, which may be the handling sleeve 98 or the activation sleeve 128. A view window 156 is provided proximally of the indication ring 154 in an initial state and out of alignment therewith. With mounting of the pen injector 14, the indication ring 154 is configured to be displaced by the pen injector 14 proximally and into alignment with the view window 156. The view window 156 is positioned to coincide with the indication ring 154 with the pen injector 14 being fully mounted to the fixturing member 22. The view window 156 provides visual indication of proper mounting of the pen injector 14. In addition to, or alternatively to, the use of the view window 156, as shown in FIG. 39, a ratchet tooth 158 and/or one or more ratchet grooves 160 may be formed on the indicator ring 154 and surrounding portions of the mixing device 10, such as on the body 46 of the fixturing member 22. In an initial state, the ratchet tooth 158 is positioned to be seated in one of the ratchet grooves 160. With proximal movement of the indication ring 154, the ratchet tooth 158 is unseated and urged into a further ratchet groove 160. The ratchet tooth 158 is configured to snap into the adjacent ratchet groove 160, thus providing an audible click and tactile response with adjustment. The ratchet tooth 158 and the ratchet grooves 160 are configured to provide audible and tactile indication with the pen injector 14 being fully mounted to the fixturing member 22. Any number of the ratchet teeth and ratchet grooves may be utilized being located on various components.

With respect to an end-of-stroke indicator for the plunger 18, and with reference to FIGS. 40-43, an indicator sleeve 162 may be seated in the second stopper 92. The indicator sleeve 162 includes a ridge 164. The plunger 18 is provided with outwardly displaceable engagement members 166 located initially proximally of the ridge 164. With the plunger 18 being driven distally to urge the flowable material 12 from the reservoir 16, force is transmitted to the second stopper 92 through the interengagment of the engagement structures 166 and the ridge 164. With the second stopper 92 coming into engagement with the first stopper 90 (FIG. 41), thus completing the stroke of the plunger 18, further force applied to the plunger 18 causes displacement of the engagement stroke members 166 over the ridge 164. Openings 168 are formed in the plunger 18 so as to be in alignment with the indicator sleeve 162 after being displaced along the indicator sleeve 162. Preferably, the indicator sleeve 162 is formed of a different color from the plunger 18 and is viewable from an external location, such as through the window 99 formed in the handling sleeve 98 via the openings 168.

The various features described herein may be used in any combination. Advantageously, the mixing device 10 may be utilized to introduce the flowable material 12 into the reservoir 24 for mixing purposes without any accommodations on, or modifications to, the pen injector 14.

What is claimed is:

1. A fixturing member for fixing a source of flowable material relative to a pen injector so as to permit introduction of the flowable material into the pen injector, the member comprising:

a body having a most proximal end and a distal end and having a web with opposing proximal and distal faces, said distal end having a distal wall extending distally from said distal face of said web, said distal wall at least partially encompassing a distal chamber, features formed on said body for removable mounting onto a pen injector, and features formed on said body for mounting onto a source of flowable material; and a cannula extending through said web, said cannula having proximal and distal ends with a lumen extending therebetween, said distal end of said cannula being located in said distal chamber and positioned such that, with the member being mounted to a pen injector, said distal end being located to be in the pen injector, said proximal end of said cannula being located proximally of said proximal face of said web and proximally of said most proximal end of said body such that, with the member being mounted to a source of flowable material, said proximal end of said cannula being located to be in communication with the flowable material.

2. A fixturing member as in claim 1, further comprising a second cannula extending through said web, said second cannula having proximal and distal ends with a lumen extending therebetween, said distal end of said second cannula being located in said distal chamber and positioned such that, with the member being mounted to a pen injector, said distal end being located to be in the pen injector, said proximal end of said second cannula being located proximally of said proximal face of said web such that, with the member being mounted to a source of flowable material, said proximal end of said second cannula being located to not be in communication with the flowable material.

3. A fixturing member as in claim 1, wherein said features for removable mounting onto a pen injector include threads.

4. A fixturing member as in claim 1, further comprising an outer sleeve disposed about a portion of said cannula so as to define exteriorly of, and along a portion of said cannula, a flow path separate from said lumen.

5. A fixturing device as in claim 1, further comprising an indented tube disposed about a portion of said cannula, said indented tube defining an outer channel along a portion of said cannula, said channel defining a flow path separate from said lumen.

6. A mixing device for introducing flowable material into a pen injector, the mixing device comprising:

a reservoir formed to accommodate a flowable material;

a displaceable plunger for urging flowable material from said reservoir;

a cannula having proximal and distal ends with a lumen extending therebetween, said proximal end being in communication with said reservoir or selectively communicatable with said reservoir; and a fixturing member having a body including a web with a distal face, a distal wall extending from said distal face of said web, said distal wall at least partially encompassing a distal chamber, an indicator, and mounting features formed on said body for removable mounting onto a pen injector, wherein said distal end of said cannula being located in said distal chamber and wherein said indicator on said fixturing member provides one or more of a visual, audible, or tactile indication that the fixturing member is mounted on said pen injector.

7. A mixing device as in claim 6, further comprising a second cannula, said second cannula having proximal and distal ends with a lumen extending therebetween, said distal end of said second cannula being located in said distal chamber, said proximal end of said second cannula not being in communication with said reservoir or selectively communicatable with said reservoir.

8. A mixing device as in claim 6, wherein said features for removable mounting onto a pen injector include threads.

9. A mixing device as in claim 6, further comprising an outer sleeve disposed about a portion of said cannula so as to define exteriorly of, and along a portion of, said cannula a flow path separate from said lumen.

10. A mixing device as in claim 6, further comprising an indented tube disposed about a portion of said cannula, said indented tube defining an outer channel along a portion of said cannula, said channel defining a flow path separate from said lumen.

11. A mixing device as in claim 6, wherein said reservoir is at least partially defined by a barrel.

12. A mixing device as in claim 11, wherein said cannula is fixed to said barrel.

13. A mixing device as in claim 11, further comprising a stopper disposed in said barrel.

14. A mixing device as in claim 13, wherein, in an initial state, said proximal end of said cannula is spaced from, or partially embedded into, said stopper, and, wherein, said stopper being displaceable to be pierced therethrough by said cannula to permit said proximal end of said cannula to be in communication with said reservoir.

15. A mixing device as in claim 13, further comprising a second stopper disposed in said barrel and spaced from said stopper, wherein said reservoir is defined between said stopper and said second stopper within said barrel.

16. A mixing device as in claim 6, further comprising biasing means for urging said plunger from a first position to a second position in urging flowable material from said reservoir.

17. A mixing device as in claim 16, further comprising releasable retaining means for releasably retaining said plunger in said first position against force of said biasing means.

18. A mixing device as in claim 17, further comprising a trigger for releasing said releasable retaining means and permitting said biasing means to urge said plunger from said first position to said second position.

19. A mixing device as in claim 6, further comprising an adjustable valve for permitting selective communication between said proximal end of said cannula and said reservoir.

20. A mixing device as in claim 6, further comprising a second indicator for indicating that said plunger has traversed a predetermined extent of movement.

21. A mixing device as in claim 6, wherein said fixturing member is fixedly attached to said reservoir.

22. A mixing device as in claim 6, wherein said fixturing member is removeably mountable to said reservoir.

23. An assembly comprising:

a mixing device as in claim 6; and, a pen injector having a reservoir formed to accommodate a secondary material, wherein said mounting features of said fixturing member being formed for removable mounting on said pen injector, wherein, with said fixturing member being mounted to said pen injector, said distal end of said cannula being located to be in communication with said reservoir of said pen injector.

24. An assembly as in claim 23, further comprising venting means for venting said reservoir of said pen injector.

* * * * *